(12) United States Patent
Uetake et al.

(10) Patent No.: US 6,708,850 B2
(45) Date of Patent: Mar. 23, 2004

(54) DISCHARGING CONTAINER WITH A FILTER AND A BOTTLE STOPPER FOR USE IN THE CONTAINER

(75) Inventors: Yorihisa Uetake, Nagoya (JP); Keiji Hamamoto, Toyono-gun (JP); Yasuyuki Shiraishi, Urayasu (JP)

(73) Assignees: Taisei Kako Co., Ltd., Osaka (JP); Nihon Tenganyaku Kenkyusyo Co., Ltd., Aichi (JP)

( * ) Notice: Subject to any disclaimer, the term of this patent is extended or adjusted under 35 U.S.C. 154(b) by 0 days.

(21) Appl. No.: 10/111,793

(22) PCT Filed: Sep. 12, 2001

(86) PCT No.: PCT/JP01/07896

§ 371 (c)(1),
(2), (4) Date: Apr. 26, 2002

(87) PCT Pub. No.: WO02/22458

PCT Pub. Date: Mar. 21, 2002

(65) Prior Publication Data

US 2002/0153386 A1 Oct. 24, 2002

(30) Foreign Application Priority Data

Sep. 12, 2000 (JP) ......................................... 2000-276130

(51) Int. Cl.[7] ................................................. B67D 5/58
(52) U.S. Cl. .................. 222/189.06; 222/105; 222/213; 222/481.5
(58) Field of Search ....................... 222/189.06, 189.09, 222/95, 105, 212, 213, 214, 215, 481.5, 494, 490, 521, 545, 546, 554

(56) References Cited

U.S. PATENT DOCUMENTS

| 3,872,866 | A | * | 3/1975 | Lelicoff ...................... 604/302 |
| 4,002,168 | A | * | 1/1977 | Petterson .................... 604/298 |
| 4,156,505 | A | * | 5/1979 | Bennett ....................... 239/327 |
| 4,646,945 | A | * | 3/1987 | Steiner et al. ............... 222/207 |
| 4,760,937 | A | * | 8/1988 | Evezich ........................ 222/95 |
| 4,776,495 | A | * | 10/1988 | Vignot ......................... 222/207 |
| 5,025,957 | A | * | 6/1991 | Ranalletta et al. ...... 222/189.09 |
| 5,082,150 | A | * | 1/1992 | Steiner et al. .......... 222/189.09 |
| 5,373,972 | A | * | 12/1994 | Bystrom et al. ............. 222/212 |
| 5,431,310 | A | * | 7/1995 | Kanner et al. ............... 222/212 |
| 5,490,938 | A | * | 2/1996 | Sawan et al. ................ 210/651 |
| 5,611,464 | A | | 3/1997 | Tsao et al. |
| 5,687,882 | A | * | 11/1997 | Mueller ....................... 222/212 |
| 5,747,083 | A | * | 5/1998 | Raymond et al. ............ 426/117 |
| 5,863,562 | A | | 1/1999 | Tsao et al. |
| 6,142,345 | A | * | 11/2000 | Laible ...................... 222/189.1 |
| 6,168,581 | B1 | * | 1/2001 | Buehler ....................... 604/295 |
| 6,336,571 | B1 | * | 1/2002 | Chibret et al. ......... 222/189.09 |
| 6,364,163 | B1 | * | 4/2002 | Mueller ........................ 222/83 |

FOREIGN PATENT DOCUMENTS

| JP | 6086341 | 6/1985 |
| JP | 44155680 | 7/1996 |
| JP | 8322911 | 12/1996 |

* cited by examiner

*Primary Examiner*—Gene Mancene
*Assistant Examiner*—Frederick C. Nicolas
(74) *Attorney, Agent, or Firm*—Wood, Phillips, Katz, Clark & Mortimer

(57) ABSTRACT

The present invention provides a discharging container whose main part is a squeeze-bottle adapted for use as eyedroppers and transparent to such a degree as required. This container has to perfectly shut off ambient air and bacteria not to flowing into a liquid content of the container so as to keep it sterilized even after unsealed for use.

The discharging container has a laminated bottle 2, and a stopper 3 attached to a finish 2a of the laminated bottle, the bottle being composed of an outer layer 21 and an inner layer 22 delaminating from the outer layer 21. A vent hole 4 is formed in the outer layer so as to introduce ambient air in between the outer and inner layers 21, 22. A discharging passage 10 is formed in the stopper 3 so as to exude through it a liquid content inside the inner layer 22, and the stopper further has a check valve 8 and a filter 7 disposed on the downstream side of the valve.

26 Claims, 3 Drawing Sheets

DISCHARGING CONTAINER WITH A FILTER AND A BOTTLE STOPPER FOR USE IN THE CONTAINER

FIELD OF THE INVENTION

The present invention relates to a discharging container having a filter and adapted for use as an aseptic eyedropper, and also to a stopper for closing the container. Particularly, the invention relates to a discharging container comprising a stopper and a laminated bottle including a delaminatable inner layer such that a liquid medicine stored therein can flow out without allowing any amount of ambient air to flow into the bottle.

BACKGROUND OF THE INVENTION

Collyria are solutions or liquid suspensions of ophthalmologic medicines, that may alternativey be dissolved or suspended in time of use. Such collyria are kept sterilized for application to conjunctival sac, and the term "collyria" used herein includes eyewashes.

Collyria are dozes to eyes that are one of the most delicate organs in ever human body, and inflamed eyes are most sensitive to foreign matters. Therefore, preparation of collyria has to be done very carefully in order to keep an aseptic condition such that not only any pathogenic bacteria are alive but also any harmless bacteria are shut out completely. Even such an aseptic condition is not satisfactory, but collyria must be prepared milch more carefully lest they should be contaminated with any pyrogens and/or any amount of insoluble foreign matters.

Generally, eyedropping squeeze-bottles (viz., eyedropping containers) contain therein collyria to be distributed to users for use as eyedroppers The bodies of such eyedropping bottles are usually formed of plastics, and proper examples thereof are polyethylenes, polypropylenes, polycarbonates, polyarylates and polyethylene terephthalates. In case of such collyrium-containers, it is very important requirements that they be transparent to such a degree as enabling visual check of foreign matters from outside, and has a low permeability for vapor so as to avoid concentration of collyria due to vaporization loss of water in the container. In addition, many proposals were made to improve the prior art eyedropping containers so as to surely prevent bacteria or the like foreign matters from entering the containers and thereby rendering them non-sterilized in usage as well as in distribution. Further, those prior proposals were designed to disinfect any bacteria accidentally present in the collyria being dropped into eyes.

For the purpose of sterilizing containers once unsealed, certain reserving agents may be added to collyria (viz., contents of the containers). Examples employable as such reserving agents are polymixin sulfates, quarternary ammonium compounds, chlorobutanols, organic mercury compounds, esters of p-hydroxybenzoic acid and alcoholic derivatives thereof. These reseving agents will, despite their excellent effect of killing microbe and bacteria, possibly cause various ophthalmogical inflammation or other serious damages after repeated use. Allergic reaction may be caused to some contact lens wearers even by reserving agents contained in low concentration.

Certain filters have been proposed to selectively remove such medically ineffective additives. These filters will remove said ineffective additives from the liquid medicine (viz., a collyrium) flowing through a dispensing passage in a bottle before discharged in a dropping manner. Japanese Patent Laying-Open Gazettes No. 4-297264 and No. 6-14972 describe such a filter that is disposed in the dispensing passage formed through each eyedropper. These prior art eyedroppers will however fail to diminish the concentration of the reserving agents sufficiently if they are contained rich enough to ensure a satisfactory sterilization effect. Since those prior art eyedroppers are of such a structure that bacteria are not shut out but carried by ambient air into the collyria, concentration of the reserving agents cannot be made low but has to be high enough to disinfect such a contaminated collyria. As a result, a noticeable amount of the reserving agents will unavoidably remain in the collyria having passed the filter before dropped.

On the other hand, Japanese Utility Model Gazette No. 63-184037 discloses a certain hydrophilic permeable membrane that is disposed in a discharging aperture through which eye drops filled in a container body arc exuded. This membrane allows the eye drops to pass through it, but stops bacteria and air not to flow into the container body. The container body in this utility model may be a tube having a depressed end, or be shaped foldable into a depressed configuration so that inner volume of said body gradually decreases as its content is consumed. In this type of prior art eyedropper, flow of ambient air into the container is prevented perfectly, protecting the liquid medicine from contamination with bacteria, thus realizing a lowest possible concentration of reserving agents to be added to said medicine. Since the container body of a monolayer structure has to deform itself plastically, it will be difficult to mold it using any plastics. Thus, aluminium tubes or the like must be used to manufacture such container bodies, thereby rendering them untransparent against the general rules prescribed for eyedroppers in the Japanese Pharmacopoeia. In addition, such container bodies that will become depressed more and more along the course of usage are difficult to stand upright during storage and less convenient to use.

An object of the present invention made in view of these drawbacks is therefor to provide a discharging container comprising a squeeze-bottle adapted for use as eyedroppers and capable of satisfying the transparency requirement. This discharging container must be improved to perfectly shut off ambient air and bacteria not to flowing into a liquid content retained in the container. This means that such container has to be kept sterilized even after unsealed for use. Another object of the invention is to provide a stopper designed to be used in such a discharging container.

DISCLOSURE OF THE INVENTION

A discharging container with a filter provided herein comprises a laminated bottle and a stopper attached to a finish of the laminated bottle, wherein the bottle is composed of an outer layer and an inner layer delaminatable therefrom. A vent hole is formed in the outer layer so as to introduce ambient air in between the outer and inner layers. A discharging passage is formed in the stopper to exude therethrough a liquid content retained inside the inner layer, with the filter being disposed together with a check valve in the discharging passage.

In use, the check valve will inhibit ambient air from entering the space defined by and in the inner layer. Consequently, the inner layer will deflate as the liquid content is consumed, with the liquid content being protected from contamination with bacteria which would otherwise be carried by ambient air into that space. Ambient air is however allowed to flow inwards in between the outer and inner layers through the vent hole, so that the outer layer once pressed with fingers or the like to exude the liquid content will restore its normal shape due to elastic recovery, until the container becomes empty. The container of the invention maintains its outer configuration unchanged from the beginning to end of usage, thereby enabling it to stand upright during storage and rendering it more convenient to use. Since the inner layer deflates and ambient air is prevented from flowing into the inner layer as mentioned above, despite gradual consumption of the liquid content, any reserving agents need not be added for the purpose of durable sterilization. Further, any resin materials may be employed to manufacture the inner and outer layers, if they are transparent to the required degree and do function as a good gas barrier and a good water vapor barrier. Thanks to these features, the container will show excellent performances as an eyedropper.

Preferably, a further check valve may be disposed in the vent hole so as to permit ambient air to flow in a space defined by and between the inner and outer layers and to prevent the ambient air having entered this space from flowing out through the outer layer. If such a further check valve is incorporated, then the squeezing of the outer layer will compress the air held in that space to raise its pressure, which in turn will depress the inner layer to exude the liquid content through the discharging passage. If contrarily no such check valve is employed, then users of this container will need to close the vent hole with their fingers or the like when they squeeze the outer layer of container.

The container of the invention has in its discharging passage the filter as discussed above, so that the bacteria floating within ambient air are stopped not to enter the bottle through said passage. Thanks to this feature, the interior of this bottle once opened will be kept sterilized even in a case wherein a very slight or no amount at all of reserving agent is added to the content. In another case wherein significant quantities of reserving agents are used to be present in the liquid content, the filter may preferably be designed such that bacteria are inhibited from passing through it and reserving agents are selectively removed from it.

The filter may be located downstreamly of the check valve first mentioned above. The liquid content portion stagnant around the check valve, particularly in the downstream side thereof, is also protected by the filter so as not to contact the ambient air. Bacteria will thus be inhibited to propagate in the stagnant portion of liquid content, thereby making it possible to secure a sufficient space between the check valve and the filter wide enough to allow the check valve to be smoothly opened and closed, with the space being protected from the breeding or propagation of bacteria.

The stopper which the present invention provides from another aspect is one to be attached to a finish of the bottle and does comprise a discharging passage for dispensing a liquid content held in the bottle, a check valve disposed in the discharging passage, and a filter also incorporated therein and located downstreamly of check valve.

The check valve may have a valve hole constituting a part of the discharging passage and a valve body for closing the valve hole from its downstream side, wherein the valve body closing the valve hole can be displaced downstreamly to open it. A free space is defined between the valve hole and the filter so as to permit displacement of the valve body.

The valve body may be formed integral with a cylindrical member, disposed between the valve hole and the filter so that this member holds the filter in place in the passage.

A deformable thin piece or pieces may connect the cylindrical member to the valve body continuing therefrom.

The filter may be formed such that bacteria are inhibited from passing from the downstream side to the upstream side of the filter.

The discharging passage may have, downstreamly of the filter, a region whose volume is not larger than one drop of the liquid content being exuded dropwise out of said passage.

The bottle may comprise a cap attachable to the bottle's finish, with a projection protruding from the cap so as to fit in and engage with the discharging passage region located downstreamly of the filter. The stopper according to the invention in this case may have, as the passage region located at downstream side of the filter, a cavity that will be fully occupied by the projection.

The check valve may be designed such that inward flow of the ambient air into the bottle is prevented but the liquid content of the bottle can flow out of the bottle.

DETAILED DESCRIPTION OF THE INVENTION

Figure 1:
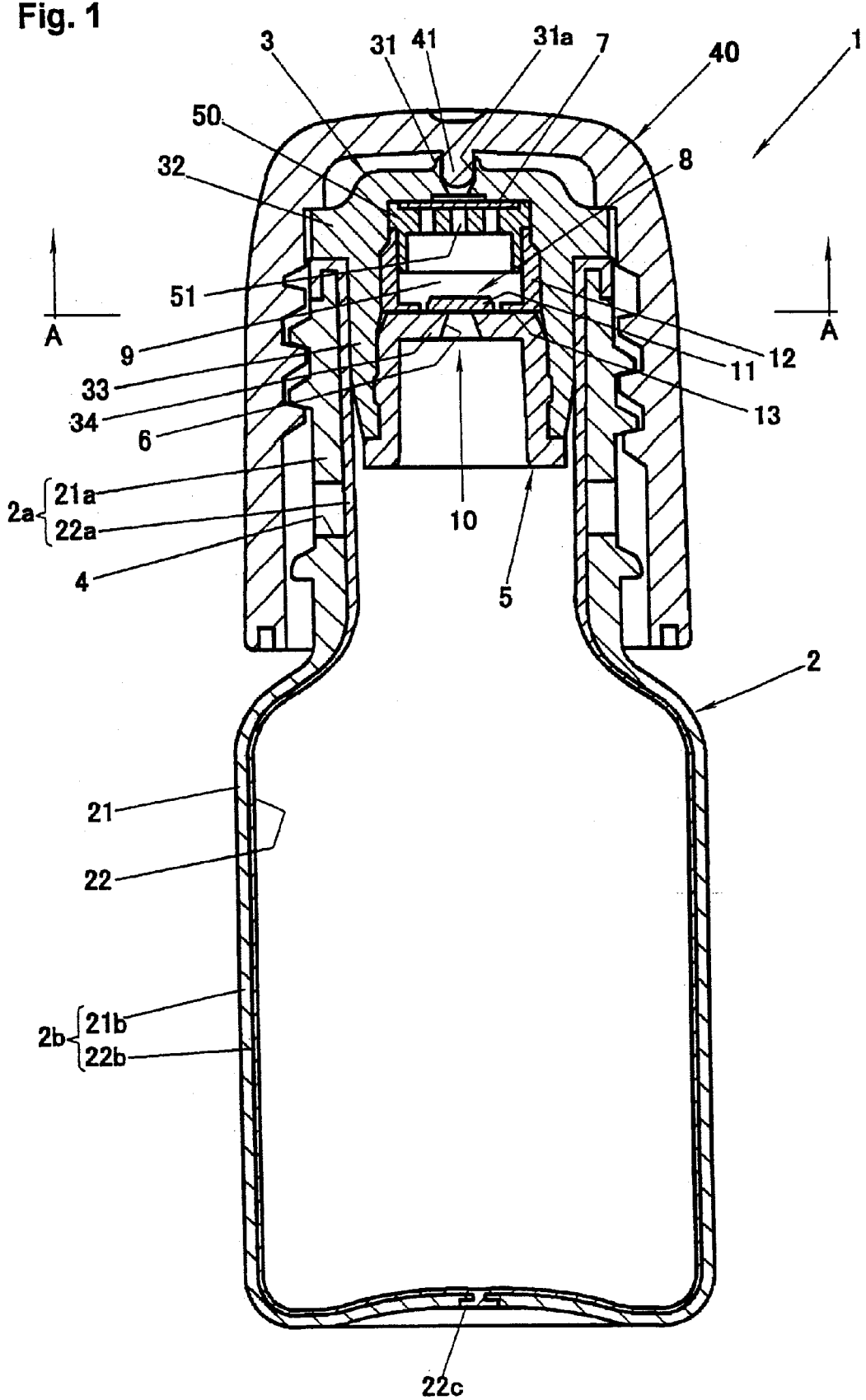
FIG. 1 is a cross-sectional side elevation of an eyedropper provided in an embodiment of the present invention.

The discharging container of the invention may be utilized as any medicine container such as an eyedropper, or as any cosmetics container or the like. The container may comprise at least the bottle and the stopper, and may additionally comprise an external cap covering the stopper and closing a discharging passage formed therein.

The delaminatable laminated bottle may substantially consist of a finish and a body, and these may be formed by the injection blow-molding method, the direct blow-molding method, the injection molding or the like proper method. An inner preform may be made as a discrete member (viz., inner parison) to be inserted in an outer preform also made already as another member (viz., outer parison). A combination of these discrete parisons (viz., a composite parison) thus prepared will then be subjected to the blow-molding process to give the delaminatable laminated bottle, so that its inner layer is laminated on its outer layer over its full height including its finish and body. The finish may preferably be made considerably thicker and more rigid than the body, by making thicker portions of the inner and outer layers to give the finish. On the other hand, bottle body may preferably be designed such that its outer layer is capable of squeezing and elastic recovery, with its inner layer forming a film ready to deflate as the liquid content is consumed. Each of such inner and outer layers may be a monolayer structure, or alternatively be of a multilayer structure.

The bottle's inner layer may be formed of any proper resin material, for example a polyolefin such as a polyethylene (PE) and a polypropylene (PP). The bottle's outer layer may also be formed of any proper resin material, for example a saturated polyester resin such as a polyethylene terephthalate (PET) and a polyethylene naphthalate (PEN), or alternatively be formed of a soft glass. In a case wherein the container is to be used as an eyedropper, those materials for the inner and outer layers are selected to make it as transparent as possible and less impermeable for water vapor. In particular, the raw material for the inner layer brought into direct contact with a medicine as the content of said container must be a resin (such as PE) of a higher chemical resistance. The raw material for the outer layer may preferably be a resin (such as PET or soft glass) that is highly transparent and less permeable for water.

The laminated bottles each consisting of an outer PET layer and an inner PE layer are suited to the so-called EO sterilization method. The most serious problem inherent in this method is that a noticeable amount of EO gas (viz., ethylene oxide gas) tends to remain in the resins forming the bottles, probably resulting in elution into the liquid content to thereby chemically reacting with components of the liquid content. PE, PP and the like are effective to diminish residue of EO and facilitate it elute, so that the inner layer made of such a PE or PP will bring a lesser quantity of EO migrated into the liquid content. A lower water permeability through the PE inner layer will suppress vaporization of water not to condense the content. The relatively thicker outer layer may be formed of a PET highly transparent and less permeable for gases and water will render the bottle as whole more transparent and less permeable for gases and water. Thus, the inner layer will be made of a material that is more resistant to chemicals, i.e., medicines as the content of the bottle, and less permeable for water. As for the outer layer, it will be made of another material facilitating its delamination from the inner layer and having a higher strength and squeezability. Different materials of different properties can be used to form the layers to give the eyedroppers of a better performance as a whole.

The vent hole preferably having a check valve incorporated therein may either be formed in a finish, a body or a bottom of the outer layer. The check valve may be of any proper structure, and for example a plug-shaped valve body may be employed to fit in the vent hole of the outer layer, or the inner layer itself may be designed to function as the check valve. In the last case, a portion of the inner layer will close the vent hole from inside in such a state that when a negative pressure is produced in the space between the outer and inner layers the atmospheric pressure in the ambient air will deform the inner layer portion inwards and open the vent hole, thus serving as a check valve. Such an inner layer portion preferably shows elastic recovery to spontaneously restore its normal state in which it closes the vent hole. In a case wherein the vent hole is formed in the finish of the outer layer, the inner layer portion for closing the vent hole may be made thicker than the body portion of this inner layer. The thinner body portion of the inner layer will deflate as the amount of content reduces during use of this container.

The vent hole having a diameter considerably smaller than the discharging passage may dispense with any check valve. The squeezed body portion of outer layer will in this case compress the air present between it and the inner layer, to consequently compress the latter to exude the content through said passage in a dropping manner. By squeezing for instance the bottle body whose content has been consumed to a considerable extent, its volume will decrease at a higher rate than the interlayer air being exhausted out of the space between the outer and inner layers, through the vent hole, which has a small diameter, for example, of about 0.1 to 0.5 mm. Thus, the interlayer air is compressed to depress the inner layer centripetally to deflate so that the content is forced outwards through the discharging passage formed in the stopper. Effective cross-sectional area of this passage may be designed much larger than the opening of said vent hole such that the resistance to the liquid content being exuded through the passage is rendered much weaker than the resistance to the air being temporarily ventilated out. Preferably, for smooth discharge of the liquid content, the first-mentioned check, valve in the discharging passage in this case may be designed not to encounter any noticeable resistance when being opened.

The stopper according to the invention may either be a one-piece member, or a composite member consisting of two or more parts. Preferably, this stopper fitted in or on the finish of bottle may comprise a discharging (viz., dropping) nozzle protruding upwards so that the discharging passage extends axially along the axis of this nozzle.

The compulsory check valve may comprise a valve body that is disposed downstream of the valve hole to be closed with this valve body. The valve hole may be formed in a partition that is formed at an upstream end or intermediate between it and downstream end of the discharging, passage. The partition may either be formed integral with the stopper, or alternatively be a discrete member to be secured thereto. The valve body normally closing the valve hole will be shifted to its downstream position to open said hole. A sufficient space for allowing such a displacement of the valve body may be provided between the valve hole and the filter. Even if any residue of the liquid content would stay in this space, bacteria is prevented from mixing in the residue, as the space is shut off from the ambient air by the filter.

The valve body may be an integral portion of a cylindrical member arranged between the valve hole and the filter. Deformable thin pieces may integrally connect the valve body to the cylindrical member, allowing this body to displace up and down relative to this member. The cylindrical member may be shaped to support the filter in place so as to afford the sufficient space noted above for the displacement of valve body.

The filter for preventing bacteria from undesirably entering the upstream side from the downstream side thereof may for example be a membrane filter, a sintered plate, a porous membrane or the like suited to this purpose.

Preferably, the discharging passage's region located downstream of the filter may be of a volume, for example of 0.05 ml or less, smaller than each drop discharged from said passage. This will contribute to diminish the quantity of liquid content prone to contact ambient air, downstreamly of the filter.

A cap for enclosing the bottle finish may have a projection shaped to fit in the discharging passage's portion located downstream of the filter. Thanks to this projection, any residue of the liquid content stagnant downstreamly of the filter will either be repelled forwards out of said passage, or forced back inwards through said filter as the cap is mounted. Thus, the mounting of the cap will completely empty the region of the passage downstream of the filter, not to permit stagnation therein of ally amount of liquid content.

BEST MODES OF CARRYING OUT THE INVENTION

Figure 2:
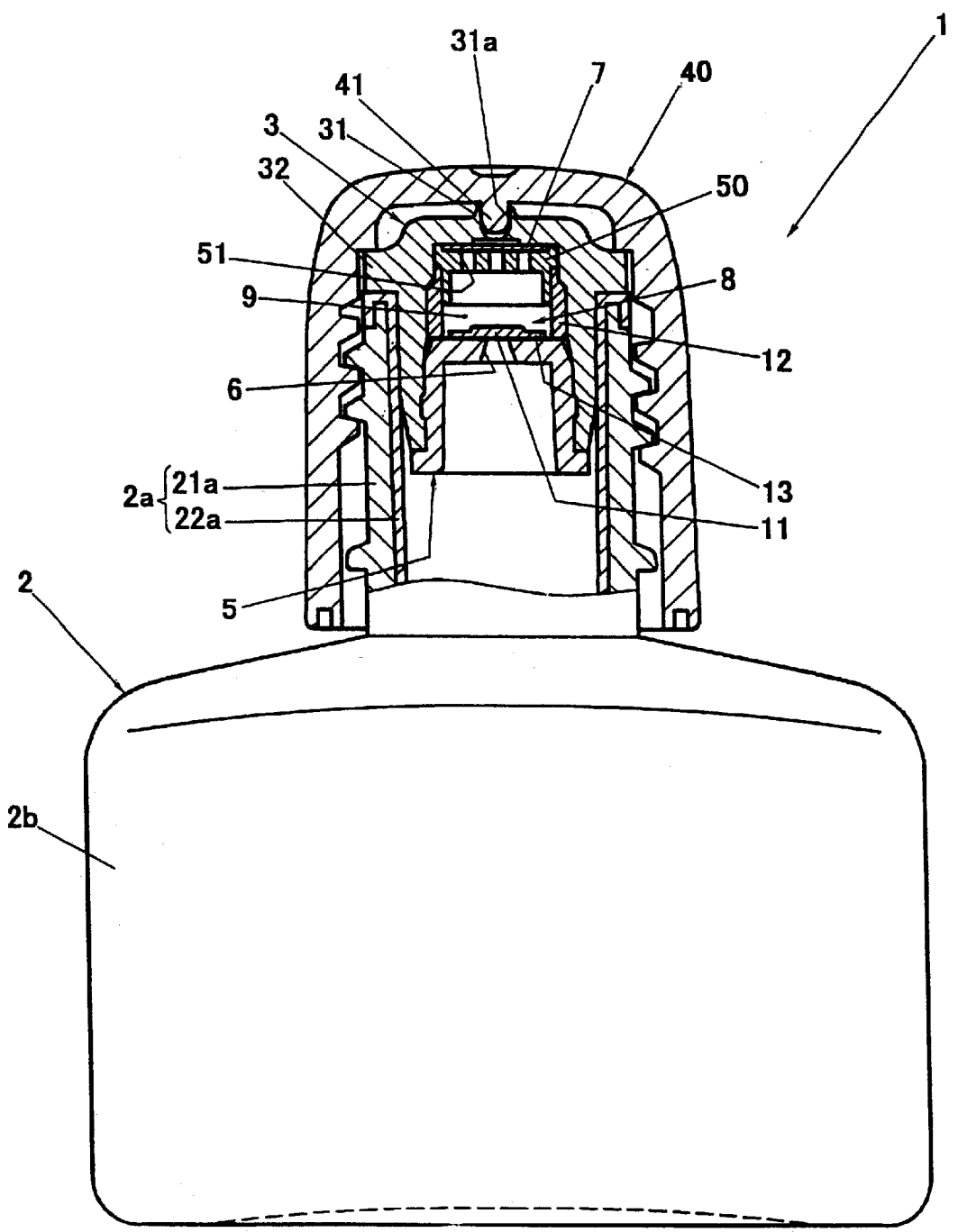
FIG. 2 is a partly fragmentary cross-sectional front elevation of the eyedropper shown in FIG. 1.

FIGS. 1 and 2 show an eyedropper 1 provided in an embodiment of the present invention. This eyedropper 1 comprises a laminated but delaminatable bottle 2 having a finish 2a and a body 2b, a plug or stopper (viz., internal cap) 3 having a dispensing nozzle 31, and a cap (viz., external cap) 40. With the body of bottle 2 being compressed by a user, a collyrium (viz., liquid content) held therein will be forced forwards through a passage 10 formed in the stopper 3, so as to be dropped off the free extremity of a discharging nozzle 31.

The delaminatable bottle 2 is composed of an outer layer 21 and an inner layer 22. Both the outer and inner layers 21 and 22 have cylindrical finish portions 21a and 22a in addition to their body regions 21b and 22b, which are oval in cross section. In other words, the bottle finish 2a is a complex of these finish portions 21a and 22a, and the body 2b being another complex of these body regions 21b and 22b. The outer layer 21 may for example be formed of a relatively hard synthetic resin such as a PET or EVOH, with the inner layer 22 being made of another resin (for example a polyolefin such as polyethylene) readily delaminating from the outer layer. An upper end of the inner layer finish portion 22a is firmly fixed on an upper end of the outer layer finish portion 21a. An inner periphery of the outer layer finish portion 21a may be knurled longitudinally of the bottle to have grooves at angular intervals so that the inner layer finish portion 22a will not become offset relative to the former portion 21a in a circular direction.

A vent hole 4 is formed in the outer layer finish portion 21a so as to introduce ambient air in between the body regions 21b and 22b of the outer and inner layer. This vent hole 4 penetrates only the outer layer 21 sideways, not the inner layer 22. A gap present between the cap 40 and the bottle 2 will serve to guide ambient air to the vent hole 4.

The inner layer body region 22b is a filmy portion ready to smoothly deflate as the amount of liquid content decreases. The inner layer finish portion 22a is thicker than the body region 22b so as to make an elastic behavior.

A part of the inner layer finish portion 22a is intended to shut from inside the vent hole 4 formed in the outer layer finish portion 21a so that the former portion does normally act as a closing member. However, said inner finish portion 22a will be pressed and deformed inwards by the atmospheric pressure to open said inlet 4 when a negative pressure is produced between the outer and inner body regions 21b and 22b, thus serving as a kind of (additional) check valve.

The inner finish portion 22a (viz., a closing portion) is of such a thickness and diameter as enabling it to recover its normal position to close the vent hole 4.

A round hook 22c formed integral at a central point of the bottom of the inner layer 22 is in a firm and tight engagement with the bottom center of the outer layer 21, thus inhibiting it from curling up.

The stopper 3 consists of the nozzle 31, a flange 32 bearing against an upper face (viz., end surface) of the bottle finish 2a, a generally cylindrical socket portion 34 and a transverse partition 33 tightly fitted therein. In the present embodiment, the nozzle 31, flange 32 and socket portion 34 are made integral with each other to be a one-piece. The partition 33 is a portion of a sealing cap 5 fitting in a lower region of the socket portion 34, and has at its center a valve hole 6.

Formed between the partition 33 and the proximal part of the nozzle 31 is a cavity or space 9 for accommodation of a filter 7 and a (compulsory) check valve 8. The interior of inner layer 22 communicates with exterior through the valve hole 6, the space 9 and an axial bore 31a extending through the nozzle 31, with these three portions or regions constituting a discharging passage 10 to discharge the liquid content in the inner layer 22.

A membrane filter is used as the filter 7 in the embodiment, though a sintered solid piece, hydrophilic or hydrophobic porous and flat membrane may alternatively be employed as such a filter. In any case, the filter 7 has to prevent permeation of bacteria and the like from the (outer) downstream side to the (inner) upstream side of the filter. This filter 7 located downstreamly of the check valve 8 and close to the nozzle 31 in the illustrated embodiment is supported by a seat 50 and held flat thereon. This seat 50 is fit in the space 9 and perforated at 51 to keep minute voids in liquid communication with the cavity 9.

The discharging bore 31a through nozzle 31 extend from the center of filter 7 to the outer (downstream) extremity of the nozzle. The bore 31a tapered towards the extremity to gradually increase its diameter does form an end region of the passage 10, located downstream of the filter 7. This end region has a volume of 0.5 ml or less corresponding to one drop of the collyrium dispensed from the nozzle opening. If the filter 7 is formed of an absorptive material, then any residual amount of collyrium will be absorbed therein to render completely vacant the bore 31a so as to more effectively avoid propagation of bacteria that would otherwise occur therein.

Figure 3:
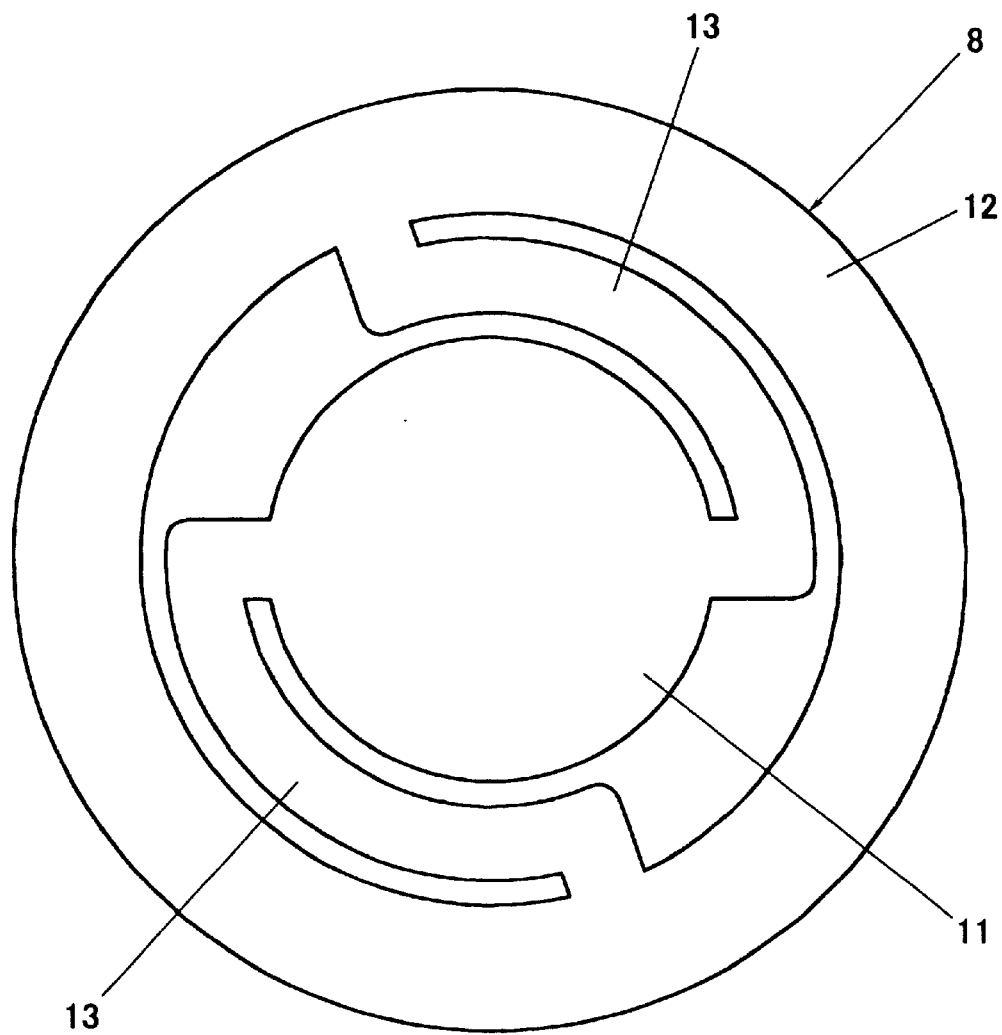
FIG. 3 is a fragmentary view seen along the arrow line A—A to show a check valve incorporated in the eyedropper of FIG. 1.

The check valve 8 comprises a valve body 11 for closing the valve hole 6 on its downstream (upper) side, which hole constituting one region of the discharging passage. This valve body 11 continues integrally through thin pieces 13 to a cylindrical member 12 intervening between the partition 33 and filter 7, in a fashion shown in FIG. 3. The cylindrical member 12 functions also to support the filter 7 in place not to move in any way within the cavity 9 (viz., passage 10). The support 50 for the filter is fitted down in an upper end of this member 12.

The external cap 40 is screwed on outer periphery of the finish 2a of bottle so that the nozzle 31 is sealed up to prevent dust and bacteria from sticking thereto. A projection 41 depending from the central inner face of the cap's top will fit in the nozzle bore 31 a so as to fully occupy it, insofar as the cap 40 remains fastened on the bottle finish 2a.

In use of the eyedropper 1 provided in the present embodiment and having its delaminatable bottle 2 filled with a collyrium, any user will grip its body 2b in a direction of its minor axis. The body regions 21b and 22b of outer and inner layers will thus be depressed in such a centripetal direction so that the collyrium held in the inner layer 22 opens the check valve 8 (by displacing its valve body 11) and drop down from the end of nozzle 31. If the user ceases to press the delaminatable bottle 2, then the outer layer 21 will recover its normal shape, with the check valve 8 being closed not to allow backflow of collyrium and flow of ambient air into the inner layer 22. This means that the inner layer 22 will never restore its original shape but continues to deflate as the collyrium is further dispensed. In more detail, as the outer layer 21 tends to restore its original shape, a negative pressure will be produced between the body regions 21b and 22b of outer and inner layers, whereby the atmospheric pressure will temporarily deform the inner layer finish 22a centripetally to consequently open the vent hole 4 formed in the outer layer 21. As a result, a sufficient amount of ambient air flows in between the inner and outer layers 22 and 21 through the vent hole 4, to thereby facilitate the outer layer body region 21b to recover its normal contour. The inner layer finish portion 22a will simultaneously get out of its temporary inward deformation so as to recover its fully cylindrical shape for keeping the vent hole 4 closed.

The user may resume his or her compressing of the delaminatable bottle 2. However, the air then present between the outer layer body 21b and inner layer body 22b will not be able to escape outwards because the inner layer finish 22a is still in close contact with the vent hole 4 to be closed. The interlayer air thus compressed by the decrease of the volume of the deformed outer layer body 21b will in turn compress the inner layer body 22b so that the remainder of collyrium is squeezed out of the inner layer 22, through the passage 10 and dropped again from the end of nozzle 31. A little amount of collyrium stays in the nozzle bore 31a after every operation of using the eyedropper, but its volume is not larger than one drop of said collyrium and it will be removed completely from said bore by mounting the cap 4 on this container.

A noticeable amount of collyrium, more or less, will stay in the space (letting the valve body 11 to reversibly open within the cylindrical member 12 in the embodiment) between the partition 34 and filter 7. However, this filter 7 will exclude the ambient air from such a stagnant amount of collyrium so as to avoid contamination thereof with bacteria, thus keeping aseptic condition.

In summary, the present invention employing resins and soft or nonrigid glasses to manufacture the bottle proposes a delaminatable structure such that its volume (inside the inner layer) will decrease as the liquid content is consumed. This structural feature excludes ambient air from entering the bottle so that it will be kept sterilized even once unsealed. This bottle can be made transparent, if necessary, to such a degree as required for eyedroppers. Further, this delaminatable bottle comprises a filter disposed on downstream side of the check valve for inhibiting inflow of ambient air, and this filter is effective to isolate from the exterior a space in which the valve opens and is closed. Thus, the liquid content stagnant in that space which is inherent in the delaminatable bottle is now rendered free from contamination with bacteria.

What is claimed is:

1. A discharging container with a filter, the container comprising a laminated bottle and stopper attached to a finish of the laminated bottle;

the bottle being composed of an outer layer and an inner layer delaminatable therefrom, with the outer layer having a vent hole formed therein so as to introduce ambient air in between the outer and inner layers, the stopper having a discharging passage formed therein to exude therethrough a liquid content inside the inner layer, the filter being disposed together with a check valve in the discharging passages, being located on a downstream side of the check valve, and being formed so that bacteria are inhibited from passing from a downstream side of the filter to an upstream side of the filter, wherein the liquid is exuded from the inner container through the discharge passage, from an upstream side of the check valve to the downstream side of the check valve, and then from the upstream side of the filter to the downstream side of the filter.

2. A discharging container as defined in claim 1, wherein the check valve has a valve hole and a valve body for closing the valve hole from its downstream side, the valve hole forming a part of the discharging passage, wherein the valve body is capable of being displaced downstreamly of the valve hole to open it, and a free space is defined between the valve hole and the filter so as to permit displacement of the valve body.

3. A discharging container as defined in claim 1, wherein the discharging passage has, downstreamly of the filter, a region whose volume is not larger than one drop of the liquid content being exuded dropwise through said passage.

4. A discharging container as defined in claim 1, further comprising a cap attachable to the finish, with a projection protruding from the cap so as to fit in and engage with a region of the discharging passage located downstreamly of the filter, to thereby occupy a cavity defined by and in the region.

5. A discharging container as defined in claim 1, wherein the inner layer spontaneously deflates as the liquid content is consumed.

6. A discharging container as defined in claim 1, wherein the outer layer of the bottle is squeezable and shows an elastic recovery.

7. A discharging container as defined in claim 1, wherein the check valve is formed to inhibit ambient air from entering a space defined by and in the inner layer, but to allow the liquid content to flow outwards.

8. A discharging container as defined in claim 1 wherein a space is defined between the check valve and the filter so as to allow the check valve to be opened and closed.

9. A discharging container as defined in claim 8, further comprising a seat in the space, wherein the filter is supported flat on the seat and the seat has a plurality of through-holes.

10. A discharging container as defined in claim 1, wherein the discharging container is an eyedropper.

11. A discharging container as defined in claim 1, wherein the discharging container is a cosmetics container.

12. A discharging container as defined in claim 1, wherein the discharging container is a medicine container.

13. A discharging container with a filter, the container comprising a laminated bottle and stopper attached to a finish of the laminated bottle;

the bottle being composed of an outer layer and an inner layer delaminatable therefrom, with the outer layer having a vent hole formed therein so as to introduce ambient air in between the outer and inner layers, the stopper having a discharging passage formed therein to exude therethrough a liquid content inside the inner layer, the filter being disposed together with a check valve in the discharging passage and being located on a downstream side of the check valve, wherein the check valve has a valve hole and a valve body for closing the valve hole from its downstream side, the valve hole forming a part of the discharging passage, wherein the valve body is formed integral with a cylindrical member disposed between the valve hole and the filter so that this member holds the filter in place in the passage and is capable of being displaced downstreamly of the valve hole to open it, and a free space is defined between the valve hole and the filter so as to permit displacement of the valve body.

14. A discharging container as defined in claim 13, further comprising at least one deformable thin piece to connect the cylindrical member to the valve body continuing therefrom.

15. A stopper to be mounted on a finish of a bottle, the stopper comprising:

a discharging passage for discharging a liquid content of the bottle from an upstream side of the discharging passage to a downstream side of the discharging passage, a discharging nozzle attached to the downstream side of the discharging passage, a check valve disposed in the discharging passage, and a filter also disposed in the discharging passage, wherein the filter is located on a downstream side of the check valve, a cavity is formed between the filter and the check valve, and the filter is formed so that bacteria are inhibited from passing from the discharging nozzle to the cavity.

16. A stopper as defined in claim 15, wherein the check valve has a valve hole and a valve body for closing the valve hole from its downstream side, the valve hole from its downstream side, the valve hole forming a part of the discharging passage, wherein the valve body is capable of being displaced downstreamly of the valve hole to open it, and a free space is defined between the valve hole and the filter so as to permit displacement of the valve body.

17. A stopper as defined in claim 15, wherein the discharging passage has, downstreamly of the filter, a region whose volume is not larger than one drop of the liquid content being exuded dropwise out of said passage.

18. A stopper as defined in claim 15, further comprising a cap attachable to the finish of the bottle, with a projection protruding from the cap so as to fit in and engage with a region of the discharging passage located downstreamly of the filter, to thereby occupy a cavity defined by and in the region.

19. A stopper as defined in claim 15, wherein the check valve is formed to inhibit ambient air from entering the space defined by and in the inner layer, but to allow the liquid content to flow outwards.

20. A stopper as defined in claim 15, wherein a space is defined between the check valve and the filter so as to allow the check valve to be opened and closed.

21. A stopper as defined in claim 20, further comprising a seat in the space, wherein the filter is supported flat on the seat and the seat has a plurality of through-holes.

22. A stopper as defined in claim 15, wherein:
the bottle is composed of an outer layer and an inner layer delaminatable therefrom, with the outer layer having a vent hole formed therein so as to introduce ambient air in between the outer and inner layers, and the inner layer spontaneously deflates as the liquid content is consumed and the outer layer of the bottle is squeezable and shows an elastic recovery.

23. A stopper to be mounted on a finish of a bottle, the stopper comprising:
a discharging passage for discharging a liquid content of the bottle,
a check valve disposed in the discharging passage, and
a filter also disposed in the discharging passage,
wherein the filter is located on a downstream side of the check valve,
wherein the check valve has a valve hole and a valve body for closing the valve hole from its downstream side, the valve hole forming a part of the discharging passage,
wherein the valve body is formed integral with a cylindrical member disposed between the valve hole and the filter so that this member holds the filter in place in the passage and is capable of being displaced downstreamly of the valve hole to open it, and a free space is defined between the valve hole and the filter so as to permit displacement of the valve body.

24. A stopper as defined in claim 23, further comprising at least one deformable thin piece to connect the cylindrical member to the valve body continuing therefrom.

25. A stopper for mounting on a finish of a bottle, the stopper comprising:
a discharging passage for discharging a liquid content of the bottle from an upstream side of the discharging passage to a downstream side of the discharging passage,
a check valve disposed in the discharging passage having a valve hole and a valve body for closing the valve hole, the valve hole forming a part of the discharging passage, wherein the valve body is capable of being displaced downstreamly of the valve hole to open the valve hole,
a filter disposed in the discharging passage on a downstream side of the check valve,
a space is defined between the valve hole and the filter so as to permit displacement of the valve body, and
a cylindrical member disposed between the valve hole and the filter and formed integral with the valve body to hold the filter in place in the passage.

26. A stopper as defined in claim 25, further comprising at least one deformable thin piece connecting the cylindrical member to the valve body continuing therefrom.

* * * * *